(12) United States Patent
Jacobson et al.

(10) Patent No.: US 10,894,529 B2
(45) Date of Patent: Jan. 19, 2021

(54) MOBILE SANITIZATION SYSTEM AND METHODS

(71) Applicants: Clifford Loren Jacobson, Paradise, CA (US); Timothy Brian Jacobson, Paradise, CA (US)

(72) Inventors: Clifford Loren Jacobson, Paradise, CA (US); Timothy Brian Jacobson, Paradise, CA (US)

( * ) Notice: Subject to any disclaimer, the term of this patent is extended or adjusted under 35 U.S.C. 154(b) by 295 days.

(21) Appl. No.: 15/857,604

(22) Filed: Dec. 28, 2017

(65) Prior Publication Data

US 2019/0202412 A1 Jul. 4, 2019

(51) Int. Cl.
*A61L 2/24* (2006.01)
*A61L 2/22* (2006.01)
*B60S 1/68* (2006.01)
*B66F 9/075* (2006.01)
*G01S 19/14* (2010.01)

(52) U.S. Cl.
CPC . *B60S 1/68* (2013.01); *A61L 2/22* (2013.01); *A61L 2/24* (2013.01); *A61L 2202/14* (2013.01); *A61L 2202/15* (2013.01); *A61L 2202/16* (2013.01); *B66F 9/07504* (2013.01); *G01S 19/14* (2013.01)

(58) Field of Classification Search
CPC .............. A61L 2/24; A61L 2/22; B60S 1/68
See application file for complete search history.

(56) References Cited

U.S. PATENT DOCUMENTS

| 6,021,959 | A | * | 2/2000 | Mayfield, Jr. | A01M 7/0014 239/67 |
| 6,450,420 | B1 | | 9/2002 | Gerber | |
| 7,043,890 | B2 | | 5/2006 | Lofton | |
| 2004/0050877 | A1 | * | 3/2004 | Ono | A61L 2/18 222/399 |
| 2007/0246564 | A1 | * | 10/2007 | Rodenbeck | E03C 1/057 239/67 |
| 2017/0173607 | A1 | * | 6/2017 | Wright | A61L 2/22 |

FOREIGN PATENT DOCUMENTS

| AU | 8662407 A | * | 12/1987 | ............... B05B 9/04 |
| JP | 2003104175 A | | 4/2003 | |
| JP | 2012050734 A | | 3/2012 | |
| JP | 2012086648 A | | 5/2012 | |
| KR | 100740681 B1 | | 7/2007 | |
| WO | 200392747 A1 | | 11/2003 | |

* cited by examiner

*Primary Examiner* — Kevin Joyner
(74) *Attorney, Agent, or Firm* — O'Banion & Ritchey LLP; John P. O'Banion

(57) ABSTRACT

A mobile sanitization system is described that allows the operator of a vehicle such as a forklift to spray a sanitizing solution onto the tires of the vehicle as it is rolling to quickly and efficiently sanitize the tires. The sanitizing solution is configured for killing any microorganisms that may be present in the tires of the vehicle, so that they are not transported into critical areas such as food processing areas.

10 Claims, 2 Drawing Sheets

MOBILE SANITIZATION SYSTEM AND METHODS

CROSS-REFERENCE TO RELATED APPLICATIONS

Not Applicable

STATEMENT REGARDING FEDERALLY SPONSORED RESEARCH OR DEVELOPMENT

Not Applicable

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to sanitization systems, and more particularly to a mobile sanitization system configured for sanitizing wheels of a conveyance or vehicle.

2. Background Discussion

Vehicles such as forklifts, carts and other wheeled conveyances are often used to carry food, materials, supplies, equipment, etc. into contaminant sensitive areas. The wheels of these vehicles, being in contact with the ground that is not clean or sanitary, often provide a source of contamination as they travel into otherwise clean or sensitive areas, e.g. for food manufacturing, processing, packaging and preparation or the like.

Accordingly, an object of the present description is a mobile sanitization system that provides rapid and focused deposition of a sanitizing solution to the wheels of vehicles prior to entering contaminant sensitive areas.

BRIEF SUMMARY

One aspect of the present description is a mobile sanitization system that allows the operator of a vehicle such as a forklift to spray a sanitizing solution onto the surface contact area or directly in front of the tires of the vehicle as it is rolling to quickly and efficiently sanitize the tires. The sanitizing solution is configured for killing any microorganisms that may be present in the tires of the vehicle, so that they are not transported into critical areas such as food processing areas. In a preferred embodiment, the sanitizing solution is configured to dry fairly quickly to limit the amount of sanitizing solution applied to the floor. This mobile sanitization system can be used to kill microorganisms that would otherwise be tracked into critical areas including food processing facilities because of the otherwise dirty tires which can transport food spoilage microorganisms and pathogens.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

Figure 1:
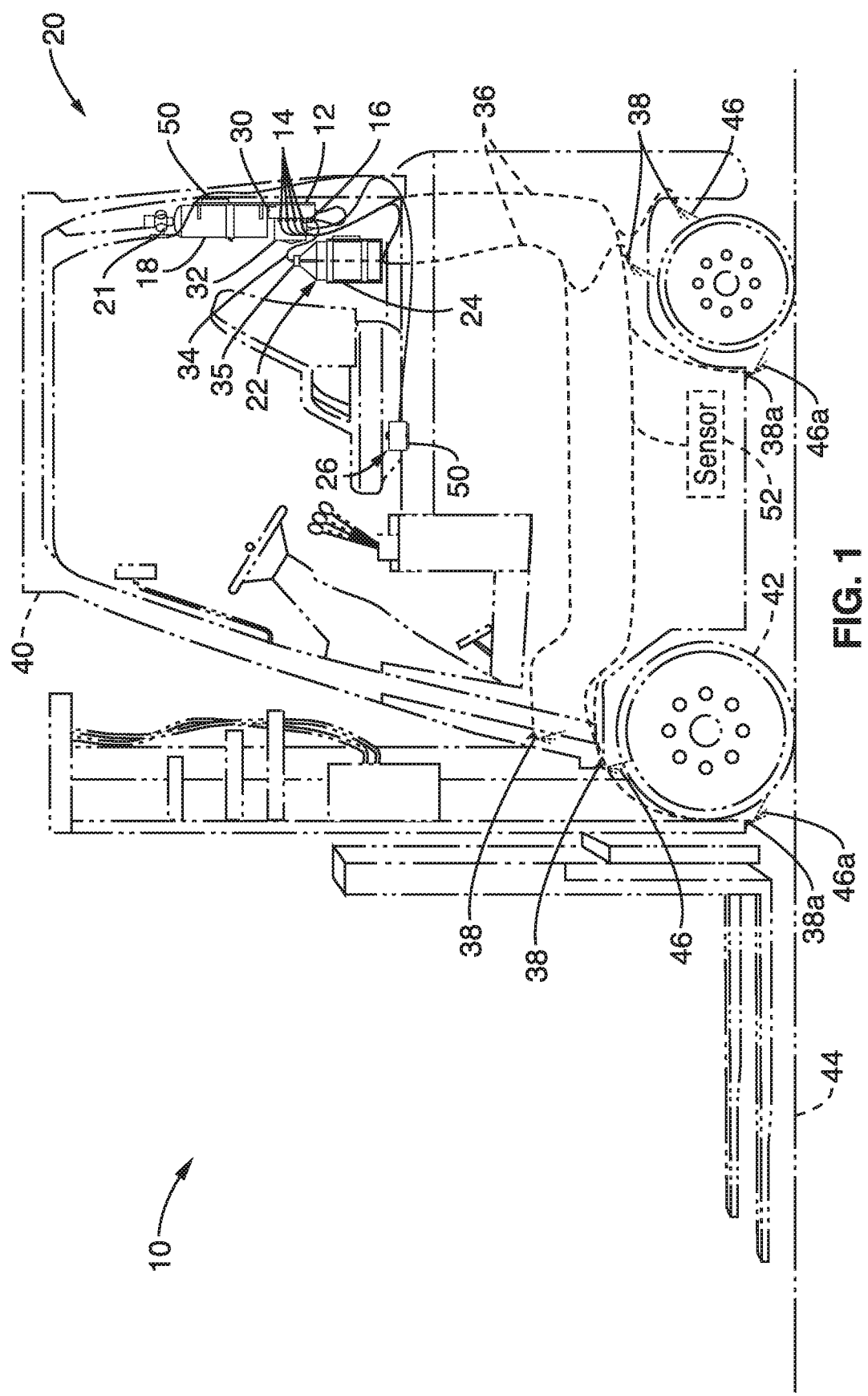
FIG. 1 is a schematic side view of the mobile sanitization system of the present invention attached to a fork lift.

The present description is directed to a mobile sanitization system for coupling to wheeled vehicles, carts and other wheeled conveyances that are used to carry food, materials, supplies, and/or equipment, etc. into contaminant sensitive areas. For purposes of the description, "wheeled vehicle" is broadly defined to mean any wheeled conveyance, whether battery/engine powered or human powered, that is used to transport people, food, materials, supplies, and/or equipment, etc. FIG. 1 details a mobile sanitization system 10 configured for attachment to a forklift 40 for sanitizing the forklift tires prior to entering a sensitive room or area, such as for food preparation. However, it is appreciated that the mobile sanitization system 10, also detailed in FIG. 2 without vehicle, may be adapted for use on any wheeled vehicle, for a variety of applications. For example, the system 10 may be used on wheeled vehicles such as utility vehicles, carts, hand trucks, gurneys, etc. for carrying food, supplies, and/or equipment into sensitive areas such as clean rooms, hospital operating rooms or the like. It is appreciated that the above list of wheeled vehicles and applications is for exemplary purposes only, and system 10 may be configured and implemented on any number of wheeled vehicles that are used in sensitive areas where contamination is a concern.

Mobile sanitization system 10 allows the operator of a vehicle 40 to spray a sanitizing solution 22 onto the tires 42 of the vehicle 40 as it is rolling, which quickly sanitizes the tires 42 to kill microorganisms so that they are not transported into sensitive areas, and then dries fairly quickly to limit the amount of sanitizing solution applied to the floor. Mobile sanitization system 10 is used to kill microorganisms that would otherwise be tracked into critical areas, as the otherwise dirty tires would transport food spoilage microorganisms and pathogens.

The core components of the mobile sanitization system 10 are a plurality of adjustable spray nozzles 38 configured to be positioned at locations at or near the wheels 42 of the vehicle 40, a pressure generating source 20 for providing motive force for delivering sanitizing solution from sanitizing solution container 22 through distribution tubing 36, and a remote activation module 26 for manual activation of the pressure generating source 20 and corresponding delivery of sanitizing solution 22 through adjustable spray nozzles 38.

Figure 2:
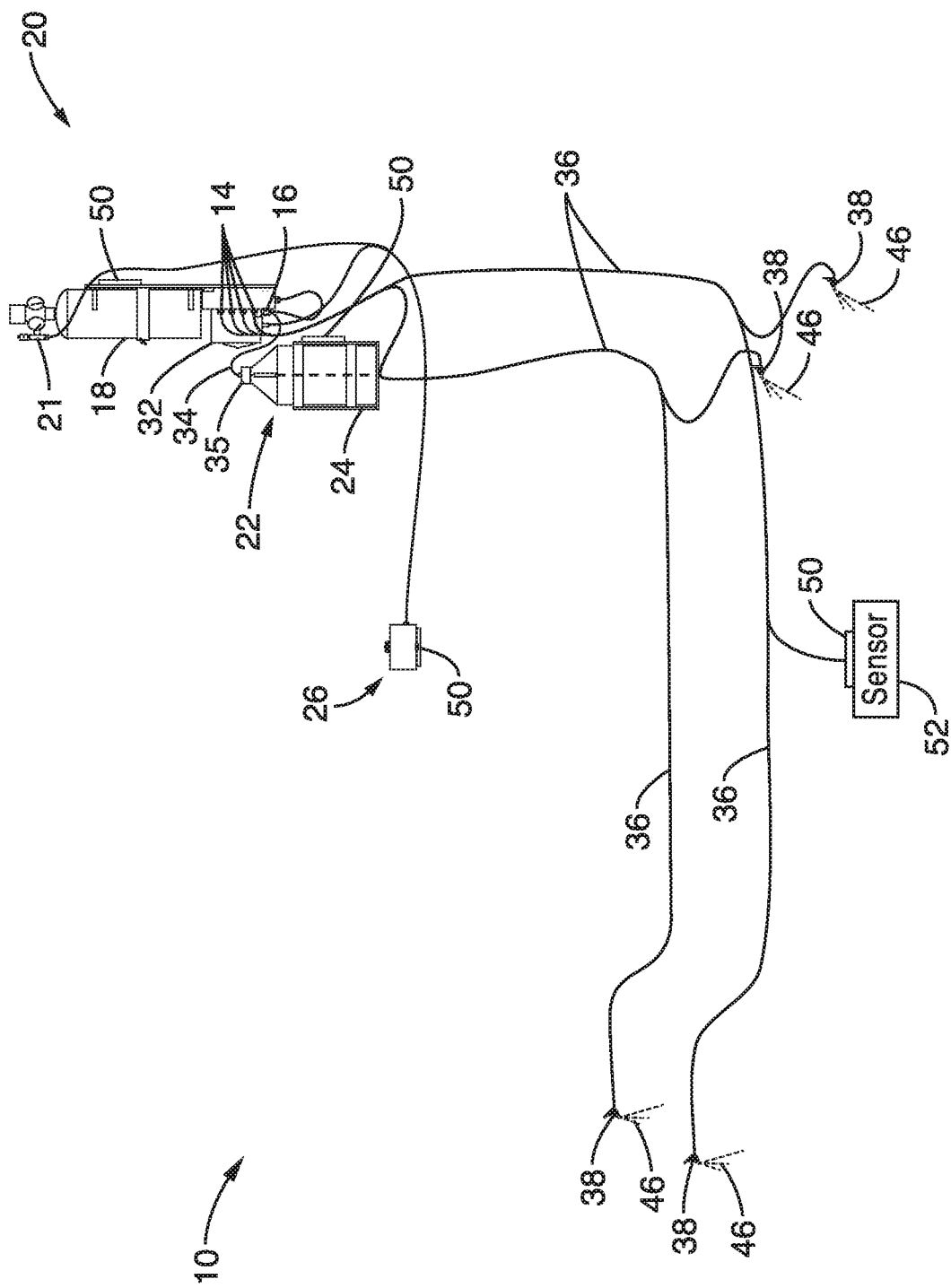
FIG. 2 is schematic side view of the mobile sanitization system of the present invention not attached to a vehicle.

In a preferred embodiment illustrated in FIG. 1 and FIG. 2, the pressure generating source 20 comprises a pressurized gas, such as $CO_2$, and associated components. The pressurized $CO_2$ gas is held in $CO_2$ tank 18, which may be supported or housed in a pressure source container bracket 30 along with a tubing distribution manifold 12 and chemical feed pump 32 (e.g. air powered diaphragm pump, or the like). The sanitizing solution container 22 may be coupled to the vehicle 40 via a dedicated solution container mounting bracket 24. Alternatively, the pressure source container bracket 30 and solution container mounting bracket 24 are integrated in a single bracket (not shown) for housing pressure generating source 20 and sanitizing solution container 22 at a single location on the vehicle 40.

In a preferred embodiment, the components (e.g. pressure source container bracket 30 and solution container mounting bracket 24, activation valve 26, and spray nozzles 38) are all attached to the vehicle 40 via a releasable attachment, such as a permanent magnet 50. It is appreciated that the releasable attachment may comprise other fastening means available in the art, e.g. bolts, screws, ties, straps, etc.

In a preferred embodiment of a mobile sanitization system 10 for use with a forklift 40, the sanitizing solution container bracket 24 is mounted in a convenient location on the vehicle, e.g. on one of the forklift upright stanchions by means of one of the permanent magnets 50, while the pressure source container bracket 30 is mounted or attached to an adjacent upright stanchion by means of one of the permanent magnets 50. The activation valve 26, (e.g. push to hold air actuating switch) is attached next to the operator seat with one of the available permanent magnets 50 in a location that can be easily accessed by the driver. The spray nozzles 38 are fastened at the vehicle wheel locations and may also be attached with the use of the permanent magnets 50 in a location to allow coverage of the resulting spray pattern 46 to the road surface of each tire. All locations shown in FIG. 1 and FIG. 2 are for illustrative purposes only, and may vary based on vehicle 40 type or user preference. E.g. for a push cart, or like wheeled vehicle (not shown), the activation valve 26 may be located on a handle (not shown) used to push the cart.

Alternatively to, or in conjunction with spray valves 38, spray valves 38a may be positioned at a location on the vehicle 40 that is configured to emit a spray pattern 46a that lands on the ground 44 just in front of or behind tires 42 (or partially on ground 44 and partially on tires 42). Chemical line check valves (not shown) or other anti-syphon type valves may be assembled in front of each of the spray nozzles 38 or 38a. The valves may be implemented to prevent dripping at the nozzles and to keep the lines primed with sanitizing solution, and or ensure that solution is only allowed to flow in one direction (outward) through the nozzles 38 or 38a.

For the pressurized-gas pressure source 20, a pressure regulator 21 (with over-pressure relief) is preferably coupled in between $CO_2$ tank 18 and the chemical feed pump 32. A feed adapter 35 may be provided to connect the ready-to-use sanitizing solution container 22 to the chemical line 34, which will feed the inlet 16 of the chemical feed pump 32.

In one embodiment, activation valve 26 comprises a push-to-hold air actuating switch that is coupled to the chemical feed pump 32, such that manual activation of the valve 26 activates chemical feed pump 32, along with pressurized $CO_2$ from $CO_2$ tank 18, to deliver the sanitizing solution to the distribution manifold 12. The distribution manifold 12 then distributes the now pressurized sanitizing solution out dedicated outlets 14 that are coupled to each of the distribution tubing lines 36. Once all of the components have been positioned in place, the provided chemical tubing line 34, airline and distribution tubing lines 36 may be fitted to each of the major components by way of push lock fittings (not shown) available in the art.

The chemical sanitizing solution 22 preferably comprises a high-alcohol content solution composed of a residual non-corrosive sanitizer configured to remain on the tire 42 surface after the alcohol has evaporated. In an alternative embodiment, the sanitizing solution 22 may comprise a water borne solution if residual moisture is not a concern, such as when used in a wet processing area.

In one exemplary method of using system 10 of FIG. 1 and FIG. 2, after completion of the installation, the sanitizing solution 22 is positioned into the chemical container rack 24 and connected by way of the chemical feed adapter 35 to the chemical feed pump 32 and the $CO_2$ tank regulator 21 is turned on and set to a pressure of approximately 20 to 30 PSI.

Ultimately, at the conclusion of the above steps, the operator is able to sanitize the wheels 42 of the vehicle 40 just prior to or while entering a controlled or contaminant-sensitive area by pushing/activating the activation valve 26 for a specified time (e.g. 2 to 3 seconds depending on vehicle 40 speed) while the vehicle is in motion, causing the ready to use sanitizing solution 22 to be dispensed through the spray nozzles 38 or 38a to surfaces 46 or 46a.

While the system 10 embodied in FIG. 1 and FIG. 2 is illustrated with use of an air ($CO_2$) driven or pneumatic system, it is appreciated that pressure source may comprise an electric fluid pump (not shown), with associated components for fluid delivery. In one embodiment, an electric pump (not shown) is used in place of the air pump 32, using low voltage instead of air to function.

In place of, or in addition to, the manual activation valve 26, an automated valve (with electrically activated switch and associated circuitry, all not shown) may be incorporated along with one or more sensors 52 to sense the location of the vehicle 40 with respect to a contaminant sensitive area. For example, sensor 52 may comprise a magnetic or RF type reader/sensor, that in conjunction with a corresponding strip (not shown) or other beacon positioned at an entryway of said sensitive area such that vehicle 40 crossing said strip is sensed by sensor 52 for automatic activation of the pressurized source 20 and delivery of sanitizing solution 22. This would eliminate, or lessen, the possibility of operator error associated with manual activation valve 26. Other sensing means, such as GPS, RF, etc. may also be employed as sensor 62).

Furthermore, the embodiments disclosed above are detailed with respect to applying the sanitizing solution at an entry of a sensitive area. It is also envisioned that the systems and methods of the present description may also be used to sanitize, disinfect, or otherwise treat a tire surface of a vehicle operating in an area known to have biohazards or contaminants so that the vehicle does not spread said contaminants to an area outside the known contaminated region upon exiting said region.

From the description herein, it will be appreciated that the present disclosure encompasses multiple embodiments which include, but are not limited to, the following:

1. An apparatus for disinfecting a surface of one or more rotating wheels of a wheeled vehicle, the apparatus comprising one or more spray nozzles; one or more attachments for attaching the one or more spray nozzles to the wheeled vehicle at locations proximate to the surface of the one or more rotating wheels; a container for holding and supplying a sanitizing solution to the one or more spray nozzles; one or more distribution lines coupled to the one or more spray nozzles and sanitizing solution container; a pressure generating source coupled to the one or more distribution lines and sanitizing solution container, the pressure generating source configured to pressurize the sanitizing solution for flow through the one or more distribution lines to the one or more spray nozzles; and an actuator coupled to the one or more distribution lines, the actuator configured to selectively release the pressurized sanitizing solution through the one or more distribution lines to the one or more spray nozzles; wherein the one or more spray nozzles and pressurized sanitizing solution are configured to provide a focused and directed spray pattern of the sanitizing solution at or near the surface of the one or more rotating wheels while the wheeled vehicle is moving to selectively apply the sanitizing solution to the surface of the one or more rotating wheels.

2. The apparatus, system or method of any of the preceding or subsequent embodiments, further comprising: a distribution manifold coupled to the one or more distribution lines, sanitizing solution container and pressure generating source; wherein the sanitizing solution is fed into an input of the distribution manifold and distributed out of the distribution manifold as a pressurized fluid through one or more dedicated outlets to the one or more distribution lines.

3. The apparatus, system or method of any of the preceding or subsequent embodiments, wherein the pressure generating source comprises a pressurized gas.

4. The apparatus, system or method of any of the preceding or subsequent embodiments, wherein the pressure generating source comprises $CO_2$.

5. The apparatus, system or method of any of the preceding or subsequent embodiments, wherein the pressure generating source and sanitizing solution container are attached to the vehicle via one or more brackets.

6. The apparatus, system or method of any of the preceding or subsequent embodiments, wherein the one or more brackets, actuator, and one or more spray nozzles are magnetically attached to the vehicle.

7. The apparatus, system or method of any of the preceding or subsequent embodiments, wherein the actuator comprises a manual switch configured to allow an operator to selectively release the pressurized sanitizing solution.

8. The apparatus, system or method of any of the preceding or subsequent embodiments, further comprising: a sensor coupled to the actuator; wherein the sensor is configured to receive location data with respect to the vehicle and automatically activate the actuator based on said location data.

9. The apparatus, system or method of any of the preceding or subsequent embodiments, further comprising: one or more check valves or anti-drip valves coupled to the one or more spray nozzles.

10. A method for disinfecting a surface of one or more rotating wheels of a wheeled vehicle, the method comprising attaching the one or more spray nozzles to the wheeled vehicle at locations proximate to the surface of the one or more rotating wheels; coupling a container holding a sanitizing solution to the one or more spray nozzles via one or more distribution lines; pressurizing the one or more distribution lines to pressurize the sanitizing solution for flow through the one or more distribution lines to the one or more spray nozzles; and selectively releasing the pressurized sanitizing solution through the through the one or more distribution lines to the one or more spray nozzles; directing a focused spray pattern of the sanitizing solution at or near the surface of the one or more rotating wheels while the wheeled vehicle is moving to selectively apply the sanitizing solution to the surface of the one or more rotating wheels.

11. The apparatus, system or method of any of the preceding or subsequent embodiments: wherein a distribution manifold and pressure generating source are coupled to the one or more distribution lines and sanitizing solution container and pressure generating source; and wherein the sanitizing solution is fed into an input of the distribution manifold and distributed out of the distribution manifold as a pressurized fluid through one or more dedicated outlets to the one or more distribution lines.

12. The apparatus, system or method of any of the preceding or subsequent embodiments, wherein the pressure generating source comprises a pressurized gas.

13. The apparatus, system or method of any of the preceding or subsequent embodiments, wherein the pressure generating source comprises $CO_2$.

14. The apparatus, system or method of any of the preceding or subsequent embodiments: wherein the pressure generating source and sanitizing solution container are attached to the vehicle via one or more brackets.

15. The apparatus, system or method of any of the preceding or subsequent embodiments, wherein the one or more brackets, actuator, and one or more spray nozzles are magnetically attached to the vehicle.

16. The apparatus, system or method of any of the preceding or subsequent embodiments, wherein selectively releasing the pressurized sanitizing solution is manually performed by a vehicle operator to selectively release the pressurized sanitizing solution.

17. The apparatus, system or method of any of the preceding or subsequent embodiments, further comprising: receiving location data with respect to the vehicle; and wherein selectively releasing the pressurized sanitizing solution comprises automatically releasing the pressurized sanitizing solution based on said location data.

18. A system for disinfecting a surface of one or more rotating wheels of a wheeled vehicle, the apparatus comprising one or more spray nozzles; one or more attachments for attaching the one or more spray nozzles to the wheeled vehicle at locations proximate to the surface of the one or more rotating wheels; a container for holding and supplying a sanitizing solution to the one or more spray nozzles; one or more distribution lines coupled to the one or more spray nozzles and sanitizing solution container; a pressure generating source coupled to the one or more distribution lines and sanitizing solution container, the pressure generating source configured to pressurize the sanitizing solution for flow through the one or more distribution lines to the one or more spray nozzles; a distribution manifold coupled to the one or more distribution lines, sanitizing solution container and pressure generating source; wherein the sanitizing solution is fed into an input of the distribution manifold and distributed out of the distribution manifold as a pressurized fluid through one or more dedicated outlets to the one or more distribution lines; and an actuator coupled to the one or more distribution lines, the actuator configured to selectively release the pressurized sanitizing solution through the one or more distribution lines to the one or more spray nozzles; wherein the one or more spray nozzles and pressurized sanitizing solution are configured to provide a focused and directed spray pattern of the sanitizing solution at or near the surface of the one or more rotating wheels while the wheeled vehicle is moving to selectively apply the sanitizing solution to the surface of the one or more rotating wheels.

19. The apparatus, system or method of any of the preceding or subsequent embodiments, wherein the actuator comprises a manual switch configured to allow an operator to selectively release the pressurized sanitizing solution.

20. The apparatus, system or method of any of the preceding or subsequent embodiments, further comprising: a sensor coupled to the actuator; wherein the sensor is configured to receive location data with respect to the vehicle and automatically activate the actuator based on said location data.

21. An apparatus for disinfecting the working surfaces of rotating wheels of a vehicle moving in a direction of travel, the apparatus comprising (a) a plurality of spray nozzles; (b) a plurality of couplings for attaching the spray nozzles to the vehicle at locations proximate to associated wheels of the vehicle and above the working surfaces of the wheels; (c) a reservoir for containing the disinfectant fluid and supplying the disinfectant fluid to the spray nozzles; (d) a fluid distribution manifold coupled to the reservoir; (e) a plurality of supply lines, wherein each supply line couples a respective spray nozzle to the distribution manifold; (f) a pressurization device configured to pressurize the disinfectant fluid for flow through the supply lines to the spray nozzles; and (g) an actuator configured to release pressurized disinfectant fluid through the supply lines to the spray nozzles; (h) wherein, when the vehicle is moving in the direction of travel and pressurized disinfectant fluid flows to the spray nozzles, disinfectant spray is released on the working surfaces of the rotating wheels.

As used herein, the singular terms "a," "an," and "the" may include plural referents unless the context clearly dictates otherwise. Reference to an object in the singular is not intended to mean "one and only one" unless explicitly so stated, but rather "one or more."

As used herein, the term "set" refers to a collection of one or more objects. Thus, for example, a set of objects can include a single object or multiple objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An apparatus for disinfecting a surface of one or more rotating wheels of a wheeled vehicle, the apparatus comprising:
    one or more spray nozzles;
    one or more attachments for reversibly attaching the one or more spray nozzles to the wheeled vehicle at locations proximate to the surface of the one or more rotating wheels;
    a container for holding and supplying a sanitizing solution to the one or more spray nozzles;
    a distribution manifold fluidly coupled to the sanitizing solution container;
    one or more distribution lines coupled to the distribution manifold and one or more spray nozzles;
    a pressure generating source coupled to the distribution manifold and sanitizing solution container, the pressure generating source configured to pressurize the sanitizing solution for flow through the one or more distribution lines to the one or more spray nozzles; and
    an actuator coupled to the one or more distribution lines, the actuator configured to selectively release the pressurized sanitizing solution through the one or more distribution lines to the one or more spray nozzles;
    wherein the sanitizing solution is fed into an input of the distribution manifold and distributed out of the distribution manifold as a pressurized fluid through one or more dedicated outlets to the one or more distribution lines;
    wherein the pressure generating source and sanitizing solution container are reversibly attached to the vehicle via one or more magnetic brackets;
    wherein the one or more brackets, actuator, and one or more spray nozzles are magnetically attached to the vehicle;
    wherein the one or more spray nozzles and pressurized sanitizing solution are configured to provide a focused and directed spray pattern of the sanitizing solution at or near the surface of the one or more rotating wheels while the wheeled vehicle is moving to selectively apply the sanitizing solution to the surface of the one or more rotating wheels.

2. The apparatus of claim 1, wherein the pressure generating source comprises a pressurized gas.

3. The apparatus of claim 2, wherein the pressure generating source comprises $CO_2$.

4. The apparatus of claim 1, wherein the pressure generating source comprises a chemical feed pump.

5. The apparatus of claim 1, wherein the actuator comprises a manual switch configured to allow an operator to selectively release the pressurized sanitizing solution.

6. The apparatus of claim 1, further comprising:
a sensor coupled to the actuator;
wherein the sensor is configured to receive location data with respect to the vehicle and automatically activate the actuator based on said location data.

7. The apparatus of claim 1, further comprising:
one or more check valves or anti-drip valves coupled to the one or more spray nozzles.

8. A system for disinfecting a surface of one or more rotating wheels of a wheeled vehicle, the apparatus comprising
one or more spray nozzles;
one or more attachments for attaching the one or more spray nozzles to the wheeled vehicle at locations proximate to the surface of the one or more rotating wheels;
a container for holding and supplying a sanitizing solution to the one or more spray nozzles;
one or more distribution lines coupled to the one or more spray nozzles and sanitizing solution container;
a pressure generating source coupled to the one or more distribution lines and sanitizing solution container, the pressure generating source configured to pressurize the sanitizing solution for flow through the one or more distribution lines to the one or more spray nozzles;
a distribution manifold coupled to the one or more distribution lines, sanitizing solution container and pressure generating source;
wherein the sanitizing solution is fed into an input of the distribution manifold and distributed out of the distribution manifold as a pressurized fluid through one or more dedicated outlets to the one or more distribution lines; and
an actuator coupled to the one or more distribution lines, the actuator configured to selectively release the pressurized sanitizing solution through the one or more distribution lines to the one or more spray nozzles;
wherein the one or more spray nozzles and pressurized sanitizing solution are configured to provide a focused and directed spray pattern of the sanitizing solution at or near the surface of the one or more rotating wheels while the wheeled vehicle is moving to selectively apply the sanitizing solution to the surface of the one or more rotating wheels.

9. The system of claim 8, wherein the actuator comprises a manual switch configured to allow an operator to selectively release the pressurized sanitizing solution.

10. The system of claim 8, further comprising:
a sensor coupled to the actuator;
wherein the sensor is configured to receive location data with respect to the vehicle and automatically activate the actuator based on said location data.

* * * * *